United States Patent [19]

Gamm

[11] 4,369,775
[45] Jan. 25, 1983

[54] MULTI-PURPOSE ANATOMICAL SUPPORT WRAP

[75] Inventor: Paul B. Gamm, Cincinnati, Ohio

[73] Assignee: Jung Products, Inc., Cincinnati, Ohio

[21] Appl. No.: 241,081

[22] Filed: Mar. 6, 1981

[51] Int. Cl.³ .............................................. A61F 13/06
[52] U.S. Cl. .................................................... 128/166
[58] Field of Search ...................... 128/165, 166, 166.5, 128/169, 157; 273/54

[56] References Cited

U.S. PATENT DOCUMENTS

| | | |
|---|---|---|
| 921,563 | 5/1909 | Quenzer . |
| 991,831 | 5/1911 | Collis . |
| 1,030,861 | 7/1912 | Anderson . |
| 1,211,055 | 1/1917 | Bernstein . |
| 1,351,248 | 8/1920 | Hill . |
| 1,389,767 | 9/1921 | Ludwig . |
| 1,441,907 | 1/1923 | Bernstein . |
| 1,443,844 | 1/1923 | Jensen . |
| 1,465,970 | 8/1923 | Cleveland et al. . |
| 1,639,198 | 8/1927 | Pease . |
| 1,741,626 | 12/1929 | Christy . |
| 2,013,757 | 9/1935 | Jung, Jr. . |
| 2,446,902 | 8/1948 | Brand . |
| 2,484,130 | 10/1949 | Thibault . |
| 2,539,170 | 1/1951 | Waite et al. . |
| 2,645,222 | 7/1953 | Capossela . |
| 3,327,703 | 6/1967 | Gamm . |
| 3,381,304 | 5/1968 | Coco . |
| 3,506,000 | 4/1970 | Baker . |
| 3,515,136 | 6/1970 | Baker . |
| 3,699,959 | 10/1972 | Garrahan et al. . |
| 3,777,751 | 12/1973 | Wise . |
| 4,085,746 | 4/1978 | Gastiglia . |

Primary Examiner—John D. Yasko
Attorney, Agent, or Firm—Wood, Herron & Evans

[57] ABSTRACT

A multi-purpose anatomical support wrap is taught comprising an elongated rectilinear strap-like body portion terminating at each of its ends in a strap-like loop. The support requires no fastening devices and can be applied to the foot as an ankle and arch support, to the hand as a support for a jammed thumb, or to the hand and upper arm near the elbow to serve as a sling.

14 Claims, 21 Drawing Figures

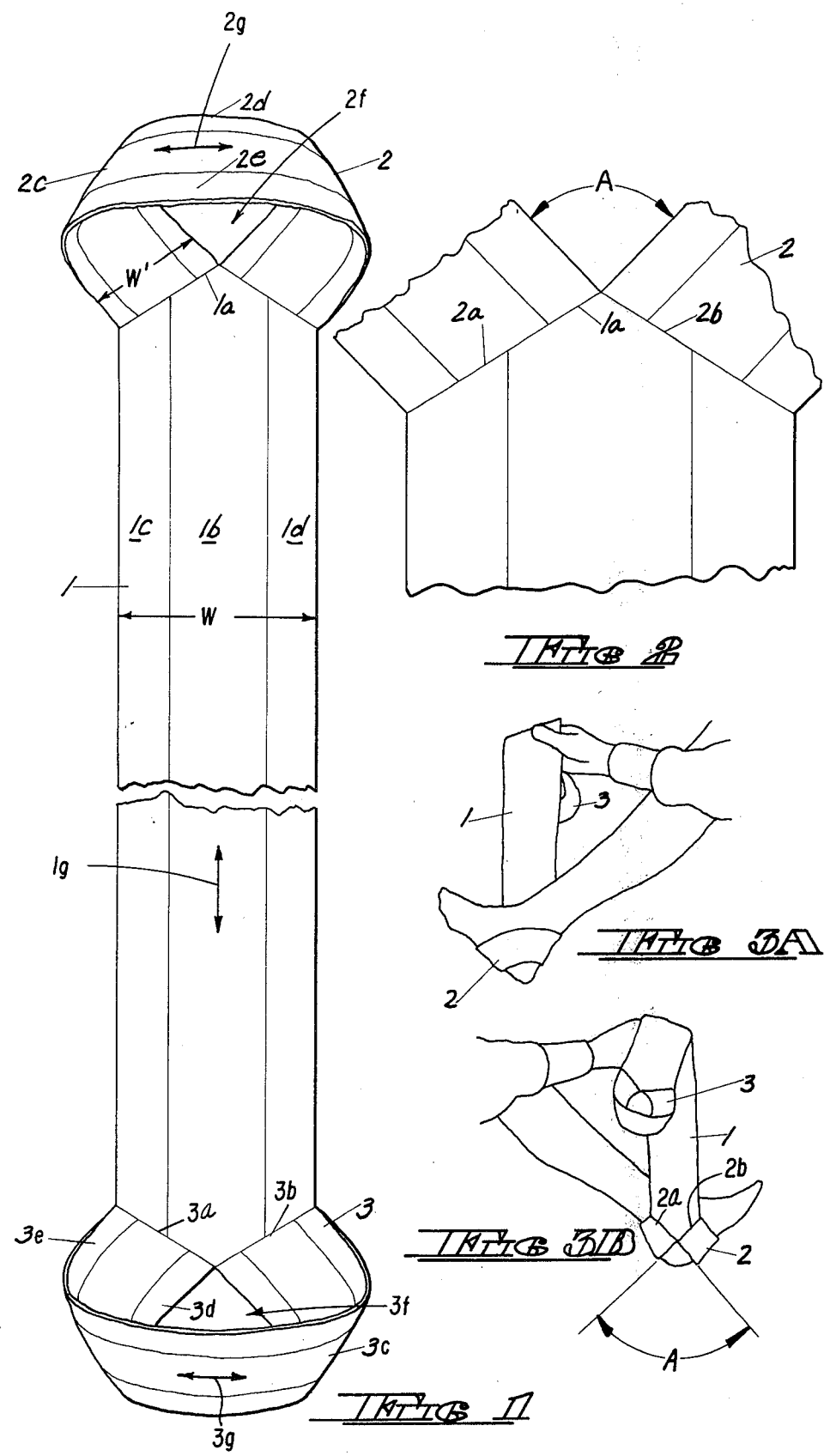

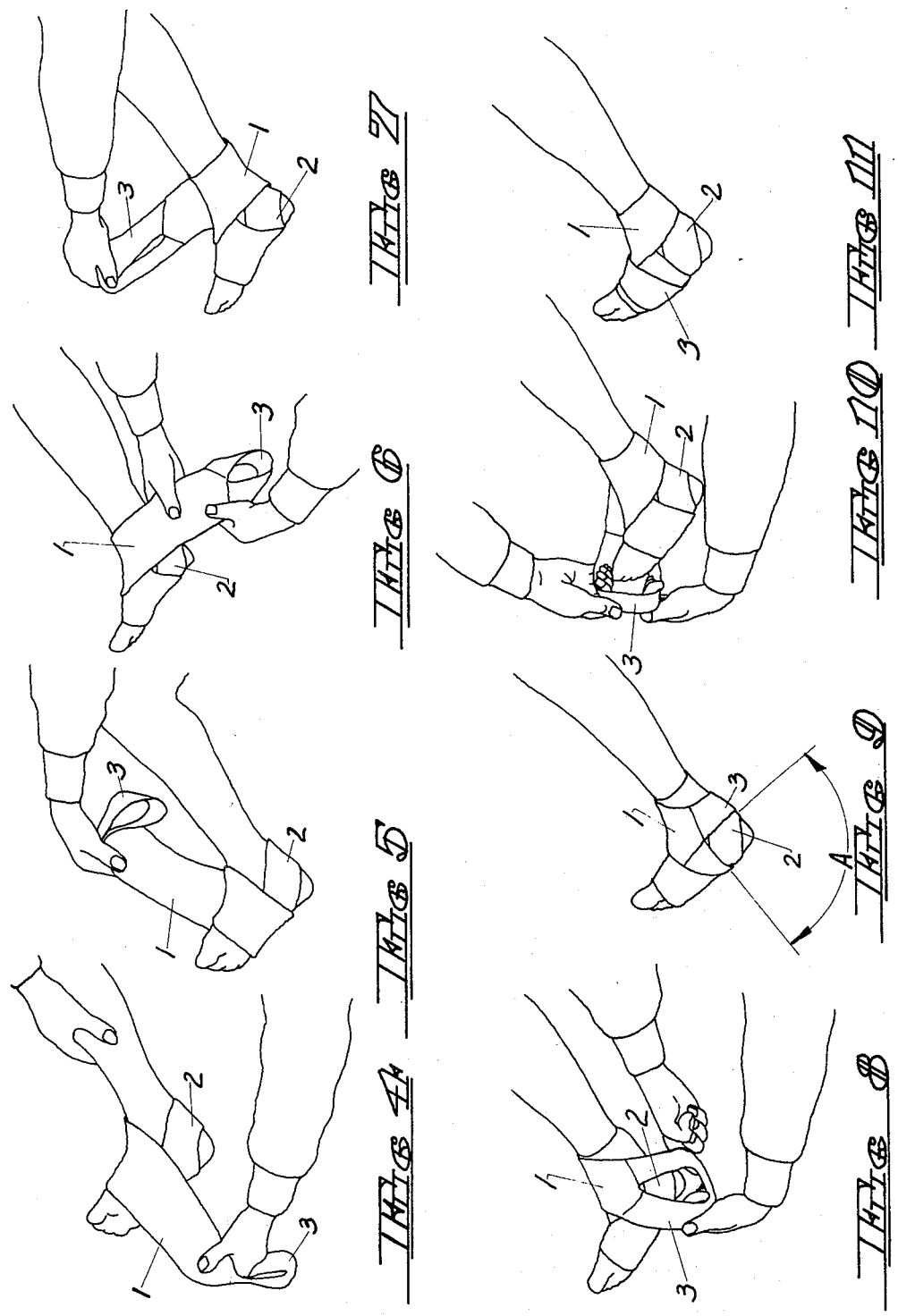

MULTI-PURPOSE ANATOMICAL SUPPORT WRAP

TECHNICAL FIELD

The invention relates to a multi-purpose anatomical support wrap, and more particularly to such a wrap which requires no fastening devices.

BACKGROUND ART

Prior art workers have devised numerous types of anatomical support wraps for application to the foot or hand. For example, U.S. Pat. No. 2,645,222 describes an ankle and foot support comprising an elongated body portion of flexible, elastic material, narrower at its midsection that at its ends, and with its ends having a particular configuration. To each end of the body portion there is affixed a specially configured end portion which, when joined to the body portion end, forms a substantially concial heel-receiving socket. At least one of the end portions is provided with a fastening means adapted to be engaged with or affixed to the body portion of the wrap once it has been applied to the foot. U.S. Pat. No. 3,777,751 teaches an ankle support constituting an elongated, inelastic body portion, provided at one end with a loop-like structure, again of inelastic material. In one embodiment, the loop-like portion is preformed and permanently affixed to the elongated body portion. In another embodiment, the loop-like portion is formed from a part of the body portion and is held in place by Velcro fastening means. When applied to the ankle, the free end of the body portion is held in place by adhesive tape or other appropriate fastening means.

The ankle supports of the above noted references are exemplary of many, all of which are characterized by the requirement for some sort of fastening means such as ties, straps and buckles, hooks, snaps, Velcro means and the like.

U.S. Pat. No. 3,381,304 teaches a hand guard or grip made of flexible material and adapted to be wrapped about the hand so as to provide a guard or grip portion at the position of the palm of the hand. In this particular instance, the device is provided with perforations at its ends through which selected fingers of the hand extend, to hold the device in place. The structure of this patent, like the ankle supports of the previously mentioned patents, is exemplary of typical prior art single-purpose wraps.

The present invention is based upon the discovery that if an anatomical wrap is made up, comprising an elongated strap-like body portion and a pair of strap-like loop portions (one affixed to each end of the body portion), the resulting structure constitutes a multi-purpose wrap. The wrap may serve as an ankle or arch support, a support for a jammed thumb or as a temporary sling, all as will be described hereinafter. Furthermore, when a portion at least or all of the device is made of elastic material, no additional fastening devices are required. In essence, the device constitutes a one-piece device with means at each of its ends to engage a body portion. These body portion engaging means serve to lock the device in place and at the same time tend to balance out each other when worn on the body. While the device of the present invention may be made in different sizes, it is otherwise universal in that the same structure is applicable to either hand or either foot in any of its uses.

DISCLOSURE OF THE INVENTION

According to the invention there is provided a multi-purpose anatomical support wrap comprising an elongated, rectilinear, strap-like body portion, terminating at each of its ends in a strap-like loop. The support wrap is a multi-purpose, one-piece device. While it may be made of flexible, inelastic material requiring means to hold it in place in at least some of its applications, preferably a part at least or all of the device is made of flexible elastic material, in which case separate fastening devices are not required.

The support wrap can be applied to either foot to serve as an ankle support. As will be described hereinafter, the support wrap can be used to relieve strain on medial or lateral ligaments of the foot and ankle, depending upon its mode of application. It is designed to hold the ankle to a minimal medial or lateral movement, while permitting maximum longitudinal movement.

The device can be applied to either hand of the user as a support means for a jammed or injured thumb. It can also be applied to the hand and upper arm of the user, near the elbow, to serve as a temporary sling.

BRIEF DESCRIPTION OF THE DRAWINGS

FIG. 1 is a fragmentary plan view of the support wrap of the present invention.

FIG. 2 is a fragmentary plan view, illustrating the junction of a looped portion of the wrap and one end of its body portion.

FIGS. 3a and 3b are fragmentary illustrations, from both sides of the users foot, depicting the first step in applying the support wrap to the foot.

FIGS. 4 through 9 are fragmentary illustrations depicting the remaining steps in applying the support wrap to the foot.

FIGS. 10 and 11 are fragmentary illustrations of the application of the support wrap as an arch support.

DETAILED DESCRIPTION OF THE INVENTION

Figure 12:
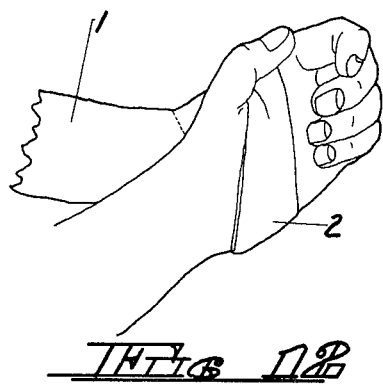
FIGS. 12 through 15 are fragmentary illustrations showing the steps in applying the support wrap of the present invention to the users hand to support a jammed or injured thumb.

Reference is first made to FIG. 1 wherein the support wrap of the present invention is most clearly shown. The support wrap comprises an elongated, rectilinear, strap-like body portion and a pair of strap-like loops 2 and 3 affixed to the ends of body portion 1. The loops 2 and 3 are preferably identical.

FIG. 2 fragmentarily illustrates the juncture of the end 1a of body portion 1 and the ends 2a and 2b of loop 2. It will be noted that the end 1a of body portion 1 is V-shaped so as to accommodate the ends 2a and 2b of loop 2. The angularity of the V-shaped end 1a of body 1 and the angularity of the ends 2a and 2b of loop 2 are so selected as to provide an included angle (designated A) between the loop ends 2a and 2b.

The loop 2 by itself forms foot or hand receiving pockets or hole 2f as shown in FIGS. 3a and 3b. It has been determined that the angle A between the ends 2a and 2b of loop 2 (see FIGS. 2 and 3b) should fall within the range of from about 70° to about 110°. When less than about 70° or more than about 110°, the loop 2 tends to slip off the heel and the support wrap will not stay in place. Preferably, angle A is about 90°.

The manner in which the loop ends 2a and 2b are joined to the end 1a of body portion 1 does not constitute a limitation on the present invention. Preferably the manner of joinder is permanent so that the overall structure constitutes a one-piece structure. The joinder may be accomplished by gluing, stitching or the like.

It will be understood that loop 3, identical to loop 2, also forms the included angle A and may be joined to the body portion 1 in a similar manner to form by itself a foot or hand receiving pocket or hole 3f.

The body portion 1 and the loops 2 and 3 may be made of any appropriate flexible strap-like material. The materials from which they are made may be inelastic, under which circumstances the support wrap will require some sort of fastening means to retain it in place. The body portion 1, on the other hand, may be made of a flexible elastic material, under which circumstances additional fastening means are not required to maintain the support wrap in place in any of its applications. Note as shown in FIG. 1, that body portion 1 is of a single width W throughout its length, that both loops 2, 3 are of the same width W' throughout their respective lengths, and that the loops' widths W' are more than 50% as wide, but less than 100% as wide, as the width W of the body portion.

The body 1 may be made of elastic material which is woven so as to have areas which exert different degrees of tension when the wrap is worn. Such material is well known in the art and is sometimes identified as dual tension elastic webbing. In such material, rubber or elastic strands extend in one direction only (i.e, lengthwise of the tension zones) so that the material is stretchable in the direction of the length of the strands, but is essentially nonstretchable transversely thereof. In other words, the body 1 is made of elastic material not substantially stretchable in a direction transverse to the longitudinal stretch direction 1g of that body. The difference in tension or elasticity in the serveral areas of the body portion may be determined by the number of rubber strands per lineal inch of webbing. The strands themselves will preferably be of the same size throughout so as to avoid detectable irregularities in the surface of the webbing. In the embodiment shown in FIG. 1, the body portion 1 has a longitudinal central zone 1b of greater tension than the longitudinal edge zones 1c and 1d when the wrap is worn. The zones 1c and 1d are of identical tensions when the wrap is worn. This arrangement assures that when the body portion 1 is stretched, it will not tend to curl transversely, particularly at the edge portions. As a result, the body portion of the support wrap, when applied to the foot, for example, will lie flat and unwrinkled against the users foot.

While not required, it is preferable that loops 2 and 3 also be made of elastic material. They too, for example, can be made of dual tension elastic. Thus, loop 2 will have a longitudinal central zone 2c of greater tension and longitudinal edge zones 2d and 2e of lesser and equal tensions. In a similar fashion, loop 3 will have a longitudinal central zone 3c of greater tension and longitudinal edge zones 3d and 3e of tensions equal to each other and less than the central zone 3c. As with the body portion 1, it is preferred that the loop portions 2, 3 each be made of elastic material not substantially stretchable in a direction transverse to the longitudinal stretch direction 2g, 3g, respectively, of the loop portions. It is also preferable that the tensions of the material from which loops 2 and 3 are made be balanced with the tensions of the body portion 1.

When used as an ankle brace or support, the support wrap of the present invention may be applied to either ankle. The support wrap is designed to relieve strain on medial or lateral ligaments of the foot and ankle. By pulling the heel initially to the outside, lateral ligaments are supported. By pulling the heel initially to the inside, medial ligaments are relieved. Since the majority of strains and sprains occur to the lateral or outside ligaments, for purposes of an exemplary demonstration of the manner in which the support wrap is applied, it will be described in terms of its application to a lateral strain or sprain of the right foot.

The first step in applying the support wrap is illustrated in FIGS. 3a and 3b. To this end, the user's heel is located in loop 2 of the support wrap with the body portion 1 of the support wrap located on the outside of the foot. It will be understood by one skilled in the art that the heel could have been located in loop 3 in the same manner, since the design of the support wrap is substantially symmetrical. An upward pull on the body portion 1 of the support wrap results in pulling the heel to the side of the injury, thereby relieving strain on the involved ligaments. As a next step, the body 1 of the wrap is brought around the foot, while pulling the wrap out to about 25% of its stretch. This is shown in FIG. 4. Thereafter, while continuing to pull the body 1 to about 25% of its stretch, the body 1 is passed beneath the foot and up the outside thereof, as shown in FIG. 5. Still under tension, the body 1 is brought across the instep, removing any wrinkles which might form, as shown in FIG. 6. Thereafter, the body 1 is passed about the ankle over the center of the heel bone as shown in FIG. 7. The body 1 is then brought again across the foot as shown in FIG. 8 and loop 3 is placed over the heel to complete the procedure, as shown in FIG. 9.

In the initial step illustrated in FIGS. 3a and 3b, the loop 2 is placed high over the heel and positioned so that the loop 2, where it joins the body portion 1 forms the desired angle A (in the exemplary embodiment about 90°). This same procedure is applied to loop 3 in the final step of the application of the support wrap, loop 3 being located high on the heel and those portions of loop 3, joining body portion 1, being arranged at the desired angle A.

To relieve a strain or sprain of the medial ligaments, exactly the same procedure is followed with the exception that in the first step loop 2 (or loop 3) is applied to the heel in such a way that the body portion 1 is located on the inside of the foot. If the support wrap of the present invention is intended to support the arch of the foot, the same procedure is followed through FIG. 7. Thereafter, the loop 3 is placed over the toes as shown in FIG. 10 and brought to a position beneath the arch of the foot, as shown in FIG. 11.

As indicated above, the support wrap of the present invention can be applied to the hand to support an injuried or jammed thumb and to maintain the thumb away from the rest of the hand. Application of the support wrap to the hand is illustrated in FIGS. 12 through 17. For purposes of an exemplary showing, the support wrap is illustrated as being applied to the left hand of the user. It will be understood that it could be applied to the right hand in precisely the same manner.

Figure 13:
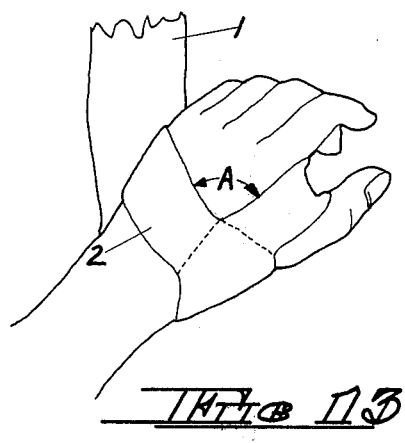
Figure 14:
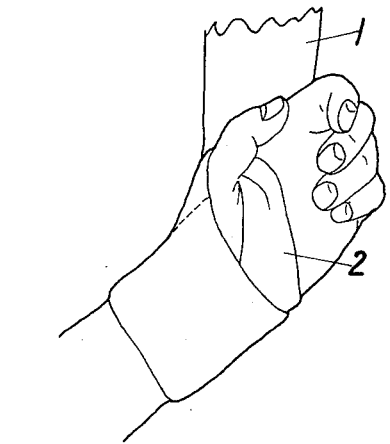
Figure 15:
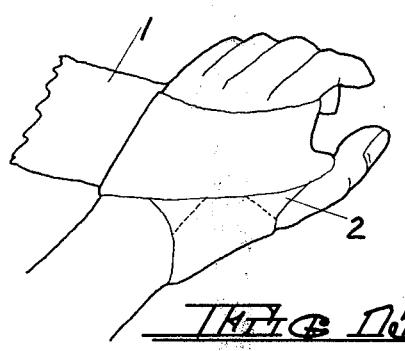
Figure 16:
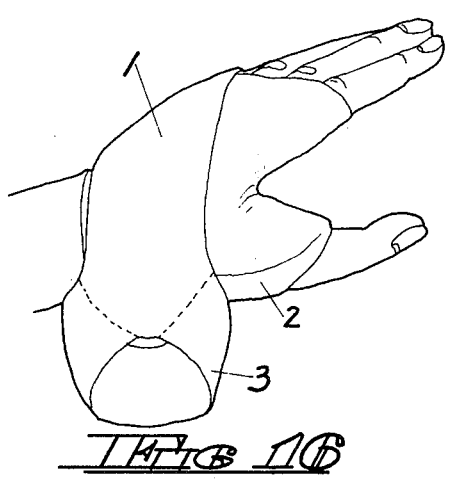
FIGS. 16 through 20 are fragmentary illustrations of the steps involved in applying the support wrap as a sling.
Figure 17:
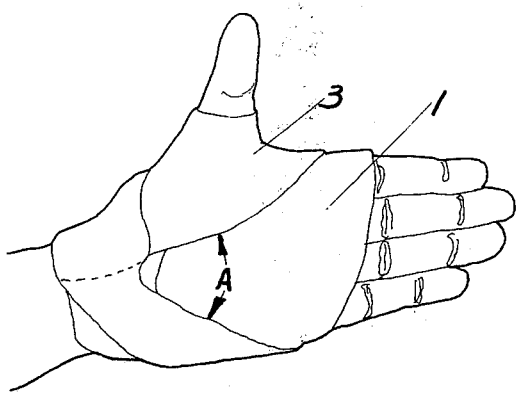

As a first step, the fingers of the hand are inserted through one of the loops of the support wraps. In FIG. 12, the fingers are shown inserted in loop 2, the loop extending across the palm of the hand and the body portion 1 located to the rear of the hand. As is shown in FIG. 13, the body portion 1 is thereafter brought about the base of the thumb and across the lower portion of the palm of the hand. This is also illustrated in FIG. 14. This Figure further illustrates that the body portion 1 is then brought across the back of the hand to a position between the thumb and the fingers. Thereafter, the body portion 1 is passed between the thumb and the fingers and again is caused to cross the palm of the hand, as shown in FIG. 15. From the position shown in FIG. 15, the body portion 1 is again brought across the back of the hand and about the base of the thumb. This is shown in FIG. 16. To complete the wrapping procedure, the loop 3 is brought forwardly of the hand and the fingers are inserted through the loop, the loop extending across the back of the hand. Since the support wrap of the present invention is preferably made in part at least of elastic material, the initial engagement of the hand in loop 2 and the final engagement of the hand in loop 3 will assure that the wrap will remain firmly in place without any additional fastening devices being required. At the same time, all but the upper portion of the thumb is engaged in the wrap with the result that the thumb will be firmly supported and held away from the rest of the hand. Again, it is preferred that the loops define the desired angle A to insure snug, nonslipping engagement with the wearer's hand.

Figure 18:
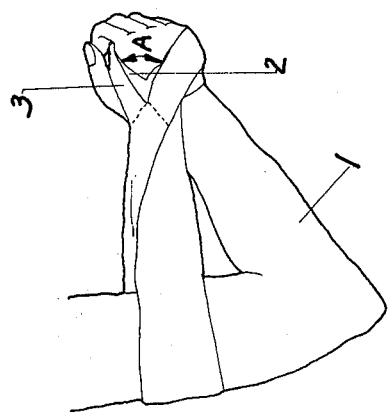
Figure 19:
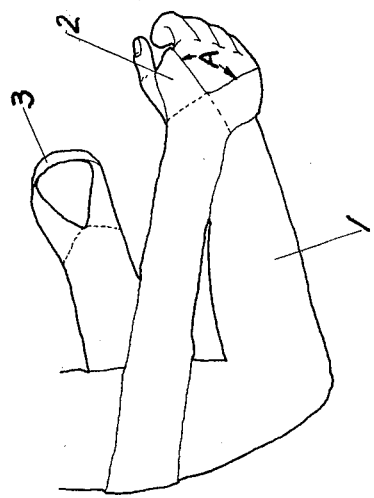
Figure 20:
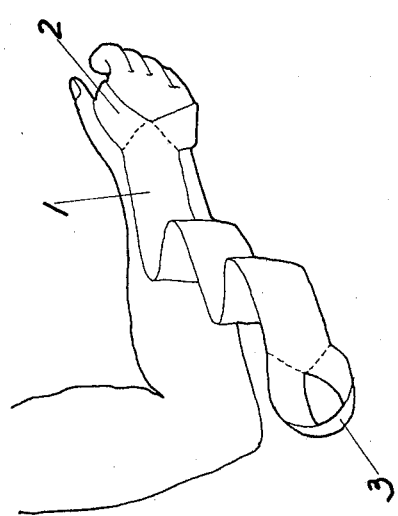

Yet another application of the support wrap of the present invention is illustrated in FIGS. 18 through 20. In this application, the device serves as a temporary sling. For purposes of an exemplary showing, the support wrap is illustrated in FIGS. 18 through 20 as being applied to the user's right hand and arm. It will again be understood that it can be applied to the left hand and arm in precisely the same manner. The first step of the application of the support wrap as a sling is illustrated in FIG. 18. The fingers of the user are inserted through one of the loops 2 or 3. For purposes of an exemplary showing, the fingers are illustrated as having been placed through loop 2, with the loop extending across the palm of the hand and with the body portion 1 of the support wrap extending from the rear of the hand. The body portion 1 is then stretched and passed about the upper arm, as shown in FIG. 19. Thereafter, the loop 3 is passed about the fingers of the hand to engage the palm of the hand, thereby completing the sling. Since both of loops 2 and 3 are engaged on the hand, the sling will be firmly held in place without the necessity of additional fastening means.

From the above, it will be evident that the support wrap of the present invention constitutes a multi-purpose wrap by virtue of its substantially symmetrical configuration, either loop can be the first to be engaged with the body portion of the user, in all three applications of the support wrap. As a result, there is no necessity to provide a left hand wrap and a right hand wrap.

The support wrap can be made in a number of different sizes. Of particular importance is the size of loops 2 and 3, especially in that use of the support wrap as an ankle wrap. If the loops are too small, they will slip off the heel and the wrap will not properly stay in place. On the other hand, if the loops are too large, they will slip up too far on the ankle and not properly hold the heel. The loops 2 and 3 should be so sized as to lie in the area of the peroneus (lateral) and flexor (medial) tendons.

Modifications may be made in the invention without departing from the spirit of it.

What is claimed is:

1. An anatomical support wrap comprising
an elongated strap like body portion having first and second ends, said body portion being made of a longitudinally stretchable material, said body portion having a longitudinal central zone and two longitudinal edge zones, and said central zone being adapted to exert a greater degree of tension than said edge zones when said wrap is stretched during use, and
first and second strap like loop portions affixed to said body portion, each of said loop portions comprising a strap like member having first and second ends, said first and second ends of each of said first loop portion being attached to said first end of said body portion, and said first and second ends of said second loop portion being attached to said second end of said body portion.

2. An anatomical wrap as set forth in claim 1, at least one of said loop portions being made of a longitudinally stretchable material.

3. An anatomical wrap as set forth in claim 2, both of said loop portions being made of a longitudinally stretchable material, neither the longitudinally stretchable material of said body portion nor the longitudinally stretchable material of said loop portions being substantially stretchable in a direction transverse to the longitudinal stretch direction of that material.

4. An anatomical wrap as set forth in claim 3, said wrap being retained in place on a user's body solely due to the stretchability of said loop portion, thereby eliminating the need for fasteners of any kind.

5. An anatomical wrap as set forth in claim 2, said stretchable loop portion having a longitudinal central zone and two longitudinal edge zones, and said central zone being adapted to exert a greater degree of tension than said edge zones when said wrap is stretched during use.

6. An anatomical wrap as set forth in claim 2, said wrap comprising a one-piece structure, said body portion being of the same width from one end to the other, said first loop portion being of the same width from one end to another, and said second loop portion being of the same width from one end to another.

7. An anatomical wrap as set forth in claim 6, said loop portions being of identical structural and tension characteristics one with the other, the width of said loop portions being more than 50% but less than 100% as wide as the width of said body portion.

8. An anatomical wrap as set forth in claim 7, said first and second ends of each of said loop portions forming an angle of about 70° to about 110° therebetween.

9. An anatomical wrap as set forth in claim 2, each of said loop portions being sized, and said body portion being of a length, to permit use of said wrap for at least two of an ankle wrap, a hand wrap, and an arm sling.

10. A method of selectively using a multi-purpose anatomical support wrap with any one of at least two of a user's foot, a user's hand, and a user's arm, said method comprising the steps of
providing a wrap comprised of an elongated strap like body portion having first and second ends, a first strap like loop portion affixed to said first end of said body portion, and a second strap like loop portion affixed to said second end of said body portion, at least said body portion being made of a longitudinal stretchable material, selecting any one of at least two of a user's foot for wrapping by said wrap, a user's hand for wrapping by said wrap, and a user's arm for bracing by said wrap, when wrapping a user's foot,
 initially inserting at least one of the toe portion of the user's foot and the heel portion of the user's foot through said first loop portion,
 subsequently wrapping at least one of the arch portion and the ankle portion of the user's foot with the wrap, and
 finally inserting the other one of the toe portion of the user's foot and the heel portion of the user's foot through said second loop portion, when wrapping a user's hand,
 initially inserting the fingers of the user's hand through said first loop portion,
 subsequently inserting the fingers of the user's hand through said second loop portion, and when bracing a user's arm,
 initially inserting the fingers of the user's hand through said first loop portion,
 directing said body portion around said user's upper arm after bending the user'2 lower arm at relatively right angles to the user's upper arm, and
 subsequently inserting the fingers of the user's hand through said second loop portion.

11. A method as set forth in claim 10, said wrap being usable with any one of a user's foot, a user's hand, and a user's arm.

12. A method as set forth in claim 11, said wrap being structured so that same can be used on either foot, on either hand, and with either arm, of a user's body.

13. A method as set forth in claim 10, when used with a user's foot, said wrap being wrappable to provide at least one of ankle support and arch support to said foot.

14. A method as set forth in claim 10, when used with a user's hand said wrap being wrappable to provide at least one of hand support and thumb support to said hand.

* * * * *

UNITED STATES PATENT AND TRADEMARK OFFICE
CERTIFICATE OF CORRECTION

PATENT NO. : 4,369,775
DATED : January 25, 1983
INVENTOR(S) : Paul B. Gamm

It is certified that error appears in the above-identified patent and that said Letters Patent is hereby corrected as shown below:

At column 2, line 66, "pockets" should be --pocket--.

At column 3, line 65, "3c" should be --3a--.

At column 8, line 4, "user'2" should be --user's--.

Signed and Sealed this

Twenty-second Day of November 1983

[SEAL]

Attest:

GERALD J. MOSSINGHOFF

Attesting Officer

Commissioner of Patents and Trademarks